(12) United States Patent
Koga et al.

(10) Patent No.: US 12,144,402 B2
(45) Date of Patent: Nov. 19, 2024

(54) WATER-SOLUBLE MALE MOLDED HOOK-AND-LOOP FASTENER AND METHOD FOR PRODUCING SAME

(71) Applicants: KURARAY FASTENING CO., LTD., Osaka (JP); KURARAY CO., LTD., Kurashiki (JP)

(72) Inventors: Nobuhiro Koga, Kurashiki (JP); Hideki Kamada, Kurashiki (JP); Satoru Ono, Okayama (JP); Yoshikatsu Fujisawa, Sakai (JP)

(73) Assignees: KURARAY FASTENING CO., LTD., Osaka (JP); KURARAY CO., LTD., Kurashiki (JP)

( * ) Notice: Subject to any disclaimer, the term of this patent is extended or adjusted under 35 U.S.C. 154(b) by 27 days.

(21) Appl. No.: 17/904,900

(22) PCT Filed: Feb. 26, 2021

(86) PCT No.: PCT/JP2021/007542
§ 371 (c)(1),
(2) Date: Aug. 24, 2022

(87) PCT Pub. No.: WO2021/172566
PCT Pub. Date: Sep. 2, 2021

(65) Prior Publication Data
US 2023/0112098 A1    Apr. 13, 2023

(30) Foreign Application Priority Data
Feb. 27, 2020  (JP) .................................. 2020-031302

(51) Int. Cl.
*A44B 18/00* (2006.01)
*A44B 13/00* (2006.01)

(52) U.S. Cl.
CPC ...... *A44B 13/0005* (2013.01); *A44B 18/0049* (2013.01); *A44B 18/0061* (2013.01)

(58) Field of Classification Search
CPC . Y10T 24/27; Y10T 24/2783; Y10T 24/2792; A44B 13/0023; A44B 13/0005;
(Continued)

(56) References Cited

U.S. PATENT DOCUMENTS

| 5,985,406 A | 11/1999 | Takizawa et al. |
| 2001/0003761 A1 | 6/2001 | Ishibashi et al. |

(Continued)

FOREIGN PATENT DOCUMENTS

| CN | 109371681 | 2/2019 |
| EP | 3949791 | 2/2022 |

(Continued)

OTHER PUBLICATIONS

English Translation of Written Opinion of the ISA as mailed May 11, 2021 and retrieved from Patentscope. (Year: 2022).*

(Continued)

*Primary Examiner* — Robert Sandy
*Assistant Examiner* — Michael S Lee
(74) *Attorney, Agent, or Firm* — Grüneberg and Myers PLLC (57) ABSTRACT

A water-soluble male-type molded hook-and-loop fastener includes a substrate and a plurality of male-type engaging elements, arranged in rows, protruding from the substrate surface. The engaging elements have a shape rising from the substrate surface and curving mid-course in a row direction, or a shape rising from the substrate surface, branching forward and backward mid-course in the row direction and curving in the row direction, with tip portions oriented toward the substrate surface in either shape. The substrate and the engaging elements both contain a mixture of a (Continued)

polyvinyl alcohol, 5 to 30 parts by mass of a polyhydric alcohol- or ethylene oxide-based polymer, and 3 to 20 parts by mass of a layered inorganic particle, based on 100 parts by mass of the polyvinyl alcohol. The polyvinyl alcohol has a degree of polymerization of 300 to 700 and a degree of saponification of 60 to 80% by mole.

12 Claims, 1 Drawing Sheet

(58) Field of Classification Search
CPC . A44B 18/00; A44B 18/0046; A44B 18/0049; A44B 18/0061
See application file for complete search history.

(56) References Cited

U.S. PATENT DOCUMENTS

| | | | |
|---|---|---|---|
| 2020/0015552 A1* | 1/2020 | Shimizu | A44B 18/0061 |
| 2022/0175093 A1 | 6/2022 | Koga et al. | |

FOREIGN PATENT DOCUMENTS

| | | | | |
|---|---|---|---|---|
| JP | H06-220287 | 8/1994 | | |
| JP | H09-313218 | 12/1997 | | |
| JP | H11-181306 | 7/1999 | | |
| JP | 2006-325939 | 12/2006 | | |
| WO | 2019/159756 | 8/2019 | | |
| WO | 2020/196722 | 10/2020 | | |
| WO | WO-2020196722 A1 * | 10/2020 | ......... | A44B 18/0049 |
| WO | WO-2021153642 A1 * | 8/2021 | | |
| WO | WO-2023276844 A1 * | 1/2023 | | |

OTHER PUBLICATIONS

English Translation of WO-2020196722-A1 produced by Clarivate (Year: 2024).*
English Translation of WO-2021153642 A1 produced by Clarivate (Year: 2024).*
English Translation of WO-2023276844-A1 produced by Clarivate (Year: 2024).*
International Search Report dated May 11, 2021, in PCT/JP2021/007542, with English translation, 5 pages.
Written Opinion dated May 11, 2021, in PCT/JP2021/007542, 6 pages.
Extended European Search Report dated Feb. 15, 2024, in European Application No. 21761450.2, 6 pages.

* cited by examiner

WATER-SOLUBLE MALE MOLDED HOOK-AND-LOOP FASTENER AND METHOD FOR PRODUCING SAME

CROSS-REFERENCE TO RELATED APPLICATIONS

This application is the National Stage entry under § 371 of International Application No. PCT/JP2021/007542, filed on Feb. 26, 2021, and which claims the benefit of priority to Japanese Application No. 2020-031302, filed on Feb. 27, 2020. The content of each of these applications is hereby incorporated by reference in its entirety.

TECHNICAL FIELD

The present invention relates to a water-soluble male-type molded hook-and-loop fastener having male-type engaging elements on a surface, a method of producing the same, and a combination of the water-soluble male-type molded hook-and-loop fastener and a water-soluble loop-type hook-and-loop fastener that can engage therewith. Specifically, the present invention relates to a water-soluble male-type hook-and-loop fastener that rapidly dissolves in normal temperature water to lose the engaging force, that has male-type engaging elements which are flexible, that does not have a breakage in the engaging elements and a crack in a substrate, and that has a high engaging force, and further has a suppressed surface tackiness, a method of producing the same, and a combination of the water-soluble male-type molded hook-and-loop fastener and a water-soluble loop-type hook-and-loop fastener that can engage therewith.

BACKGROUND ART

As one of means for attaching an object to a surface of an article, a method has conventionally been used in which a male-type hook-and-loop fastener having hook-type or mushroom-type male-type engaging elements is fixed to a surface of one of the article and the object, a loop-type hook-and-loop fastener having loop-type engaging elements is fixed to a surface of the other thereof, and the engaging element surfaces of the two hook-and-loop fasteners are superposed on each other to allow the engaging elements of the two fasteners to engage with each other, thereby fixing the object to the surface of the article. Such a fastener is conveniently used as an attaching means since attaching and detaching can be performed many times by repeating engaging and peeling and the attaching position, if is not correctly achieved at first, can be easily adjusted by peeling the fastener.

Such a hook-and-loop fastener has recently been used for fixing a sanitary good to underwear, or fixing a lumbar part of a disposable diaper. If the hook-and-loop fastener has water solubility, by making a sanitary good or a disposable diaper of a water-disintegrable nonwoven fabric or the like, the sanitary good or disposable diaper after use can be thrown into a flush toilet as it is. In addition, there is an application in which by throwing an article fastened with a hook-and-loop fastener into water, the fastened state by the hook-and-loop fastener is lost to expand the article in water or on a water surface, whereby the article fulfills the function. As a hook-and-loop fastener to be used in such an application, one that rapidly dissolves when coming into contact with water is expected to be used in a wider range of application.

Furthermore, when a male-type hook-and-loop fastener and a loop-type hook-and-loop fastener which constitute a hook-and-loop fastener are both soluble in water, the rate of the fastener to dissolve in water to lose the engaging force can be further increased. In addition, if a resin constituting the hook-and-loop fastener is a resin that is biodegradable after dissolution, this is environmentally friendly and meets social needs.

Based on the above demand, a hook-and-loop fastener having a high rate of dissolution in water is desired. Among such hook-and-loop fasteners, a loop-type hook-and-loop fastener having loop-type engaging elements can be easily obtained by using a water-disintegrable nonwoven fabric having loop-shaped fibers on the surface. However, regarding a male-type hook-and-loop fastener having male-type engaging elements, it is difficult to produce one that can rapidly dissolve in normal temperature water and has a sufficient engaging force, and no water-soluble male-type hook-and-loop fastener that meets the demand is commercially available now. In addition, no loop-type hook-and-loop fastener made of a water-soluble fiber that loses the engaging force more rapidly than the water-disintegrable nonwoven fabric has yet been commercially available.

However, an attempt has long been made to obtain a water-soluble male-type hook-and-loop fastener. For example, PTL 1 discloses, as a water-soluble male-type hook-and-loop fastener, a molded male-type hook-and-loop fastener formed of a water-soluble resin such as a water-soluble polyvinyl alcohol. However, in this document, such a water-soluble polyvinyl alcohol is not specifically described.

A polyvinyl alcohol resin has a feature of providing a fiber superior in strength and other physical properties by wet spinning or dry spinning, but has a big problem in melt molding as follows. Since polyvinyl alcohol has a decomposition temperature and a melting temperature that are very close to each other, when polyvinyl alcohol is heated merely for melting in melt molding, decomposition or gelling occurs before melting, resulting in failure of melt molding, so that a desired molded product cannot be obtained. In particular, when a molded product is a small one such as a male-type engaging element, the problem of decomposition and gelling is largely concerned. Even if a film layer of a substrate is obtained, it is difficult to obtain a male-type molded hook-and-loop fastener in which many male-type engaging elements on the surface extend to the tip portion without breaking in mid-course.

PTL 2 discloses use of a water-soluble resin obtained by graft-polymerizing a polyoxyalkylene into a copolymer of vinyl alcohol and allyl alcohol for a water-soluble molded hook-and-loop fastener suitably used in a disposable product. However, such an intricately-copolymerized water-soluble resin is not sold and not easily available now. Moreover, when a male-type molded hook-and-loop fastener is produced by using a resin similar to the intricately-copolymerized resin, the moldability is not always satisfactory and in the case of a fine male-type engaging elements, it is difficult to obtain engaging elements extending to the tip portions. In addition, the obtained molded product has a high hardness, and a small engaging element easily breaks. Furthermore, the obtained male-type molded hook-and-loop fastener is liable to have a tacky surface and is not acceptable. In actual, a water-soluble male-type molded hook-and-loop fastener formed of the resin as described in PTL 2 has not been produced or sold.

In addition, PTL 1 also describes a woven fabric-type hook-and-loop fastener made of a water-soluble fiber as a water-soluble male-type hook-and-loop fastener. In the case of a woven fabric-type hook-and-loop fastener, a male-type engaging element is a hook-shaped one made of a monofilament. A monofilament formed of a water-soluble polyvinyl alcohol is poor in the thermosetting property, and as a result, weak engagement allows the hook shape to easily stretch to release the engagement, whereby a sufficient engaging force cannot be achieved. When a polyvinyl alcohol having a high thermosetting property is used for preventing this, the obtained hook-and-loop fastener is not soluble in normal temperature water.

CITATION LIST

Patent Literature

PTL 1: JP 2006-325939 A
PTL 2: JP 9-313218 A

SUMMARY OF INVENTION

Technical Problem

The present invention has an object to provide a water-soluble male-type molded hook-and-loop fastener which rapidly dissolves in normal temperature water, which has flexible male-type engaging elements, in which gelling and decomposition during molding of a resin used for molding is suppressed, resulting in rarely having a breakage of the male-type engaging element and a crack or the like in a substrate layer, and which has a high engaging force and a suppressed surface tackiness, and a method of producing the same, and also to provide a combination of the water-soluble male-type molded hook-and-loop fastener and a water-soluble loop-type hook-and-loop fastener that can engage therewith. Preferably, the present invention has an object to provide a water-soluble male-type molded hook-and-loop fastener in which the aforementioned performance is almost not deteriorated even if the water-soluble male-type molded hook-and-loop fastener has small male-type engaging elements which are inferior in moldability.

Solution to Problem

Specifically, the present invention relates to a water-soluble male-type molded hook-and-loop fastener including a substrate and a plurality of male-type engaging elements protruding from a surface of the substrate, the water-soluble male-type molded hook-and-loop fastener satisfying the following (1) to (3):
(1) the plurality of male-type engaging elements are arranged in rows, and each of the engaging elements has a shape in which the element rises from the substrate surface, curves, in mid-course, in a row direction so that a tip portion thereof is oriented toward the substrate surface, or each of the engaging elements has a shape in which the element rises from the substrate surface, branches in mid-course forward and backward in the row direction so as to curve in the row direction so that each branched tip portion is oriented toward the substrate surface,
(2) the substrate and the male-type engaging elements both contain a mixture of a polyvinyl alcohol, a polyhydric alcohol- or ethylene oxide-based polymer, and a layered inorganic particle, the polyhydric alcohol- or ethylene oxide-based polymer being mixed in a proportion in the range of 5 to 30 parts by mass and the layered inorganic particle being mixed in a proportion of in the range of 3 to 20 parts by mass based on 100 parts by mass of the polyvinyl alcohol, and
(3) the polyvinyl alcohol has a degree of polymerization of 300 to 700 and a degree of saponification of 60 to 80% by mole;
and in a preferred case of such a water-soluble male-type molded hook-and-loop fastener, when each of the male-type engaging elements has a shape in which the element rises from the substrate surface, curves, in mid-course, in the row direction so that a tip portion thereof is oriented toward the substrate surface, the male-type engaging element has a height from the substrate surface to a top of the male-type engaging element of 1.2 mm or less, and when each of the male-type engaging elements has a shape in which the element branches in mid-course forward and backward in the row direction so as to curve in the row direction so that each branched tip portion is oriented toward the substrate surface, the male-type engaging element has a height from the substrate surface to a top of the male-type engaging element of 0.6 mm or less.

Preferred cases of the water-soluble male-type molded hook-and-loop fastener are a case in which the polyhydric alcohol- or ethylene oxide-based polymer is a polyethylene glycol, the polyethylene glycol having a number average molecular weight of 300 to 700, a case in which the layered inorganic particle is talc, a case in which the water-soluble male-type molded hook-and-loop fastener has such a water solubility as to completely dissolve in water at 25° C. within 20 minutes, or a case in which 98% or more of the male-type engaging elements each have a tip portion that is oriented toward the substrate surface without ending in mid-course.

The present invention further relates to a combination of the water-soluble male-type molded hook-and-loop fastener and a water-soluble loop-type hook-and-loop fastener made of a water-soluble fiber. In a preferred case of the combination, the water-soluble loop-type hook-and-loop fastener is a nonwoven fabric made of a polyvinyl alcohol-based fiber, and has loops made of the same fiber on a surface thereof.

The present invention also relates to a method of producing a water-soluble male-type molded hook-and-loop fastener, the method including pouring a molten product of a mixture that satisfies the following (4) and (5) onto a surface of a metal roll that satisfies the following (A) while press-filling the molten product into cavities each having a male-type engaging element-shape perforated in the metal roll surface, cooling and solidifying the molten product as it is, and then peeling the solidified product from the metal roll surface while pulling the solidified product out of the cavities:
(A) the metal roll is thin ring-shaped dies superposed, the thin ring-shaped dies each having a plurality of male-type engaging element-shaped cavities engraved on an outer circumference thereof, a plurality of cavities for male-type engaging element are arranged in rows on a surface of the metal roll in a circumferential direction of the roll, each of the cavities curves, in mid-course, in a cavity-row direction so that a tip portion thereof approaches the metal roll surface, or each of the cavities branches in mid-course into two lines so as to curve in the row direction so that each tip portion thereof approaches the metal roll surface,
(4) the mixture contains a mixture of a polyvinyl alcohol, a polyhydric alcohol- or ethylene oxide-based polymer, and a layered inorganic particle, the polyhydric alcohol- or ethylene oxide-based polymer being mixed in a proportion in the range of 5 to 30 parts by mass and the layered inorganic particle being mixed in a proportion in the range of 3 to 20 parts by mass based on 100 parts by mass of the polyvinyl alcohol, and (5) the polyvinyl alcohol has a degree of polymerization of 300 to 700 and a degree of saponification of 60 to 80% by mole, and in a preferred case of the method of producing a water-soluble male-type molded hook-and-loop fastener, when each of the cavities has a shape in which the cavity curves, in mid-course, in a cavity-row direction so that a tip portion thereof approaches the metal roll surface, the cavity has a largest depth from the metal roll surface of 1.2 mm or less, and when each of the cavities has a shape in which the cavity branches in mid-course into two lines so as to curve in the row direction so that each tip portion thereof approaches the metal roll surface, the cavity has a largest depth from the metal roll surface of 0.6 mm or less.

Advantageous Effects of Invention

In the present invention, a resin composition used in molding is constituted of a specific polyvinyl alcohol, a polyhydric alcohol- or ethylene oxide-based polymer, and a layered inorganic particle, and the components are mixed in amounts of a specific ratio. Use of such a specific resin composition makes it possible to obtain a water-soluble male-type molded hook-and-loop fastener that can rapidly dissolve in normal temperature water. In addition, such a specific resin composition rarely undergoes gelling and decomposition under a melt-molding condition, and is superior in moldability, and as a result, a breakage in a male-type engaging element and a crack and the like in a substrate layer are rarely caused in molding. Furthermore, the obtained male-type molded hook-and-loop fastener is flexible, and also in this point, a breakage in a male-type engaging element and a crack in a substrate layer are rarely caused. In addition, in the molded hook-and-loop fastener obtained in the present invention, the layered inorganic particle which is added enhances moldability and can suppress tackiness of a hook-and-loop fastener surface so that the molded hook-and-loop fastener can be used in an environment with a high humidity with no problem.

In addition, for the male-type molded hook-and-loop fastener of the present invention, a method is used which includes pouring a molten product of the specific resin composition as described above onto a surface of the metal roll as described above while press-filling the molten product into male-type engaging element-shaped cavities perforated in rows in the metal roll surface, cooling and solidifying the molten product as it is, and then peeling the solidified product from the metal roll surface while pulling the solidified product out of the cavities. As a result, the obtained water-soluble male-type molded hook-and-loop fastener has a plurality of male-type engaging elements which are arranged in rows, each of the engaging elements having a shape in which the element rises from the substrate surface, curves, in mid-course, in the row direction so that a tip portion thereof is oriented toward the substrate surface (this shape is hereinafter sometimes referred to as inverted J-shape), or each of the engaging elements having a shape in which the element rises from the substrate surface, branches in mid-course forward and backward in the row direction so as to curve in the row direction so that each branched tip portion is oriented toward the substrate surface (this shape is hereinafter sometimes referred to as Y-shape).

In such male-type engaging elements, the curving direction is uniform, and the male-type engaging elements cooperatively resist the pulling in the engaging element-row direction by the elements to be engaged. Thus, the male-type engaging elements are less likely to break, and a high engaging force is more easily achieved as compared with the case in which head portions of engaging elements (expanded head portions for engagement) extend in a direction to intersect with the engaging element rows or the case in which tip portions of stems expand in an umbrella shape as in other male-type molded hook-and-loop fasteners. In the present invention, particular when the height of the male-type engaging elements is low, in conjunction with the flexibility of the male-type engaging elements, the foreign-body sensation can be suppressed and rough skin is less likely to be caused in contact with the skin even in attachment to a part of a sanitary good or the like that often comes in contact with the skin, and in addition, the time required for dissolution can be reduced more.

Furthermore, since the polyvinyl alcohol, the polyhydric alcohol- or ethylene oxide-based polymer, and the layered inorganic particle which constitute the water-soluble male-type molded hook-and-loop fastener of the present invention are all largely used in an application involved in a contact with the human skin, the water-soluble male-type molded hook-and-loop fastener of the present invention hardly inflicts harm on the human body.

DESCRIPTION OF EMBODIMENTS

Next, the water-soluble male-type molded hook-and-loop fastener of the present invention and the method of producing the same will be described in detail. First, the water-soluble male-type molded hook-and-loop fastener of the present invention is constituted of a specific polyvinyl alcohol resin, a polyhydric alcohol- or ethylene oxide-based polymer, and a layered inorganic particle, as described above.

Among them, the polyvinyl alcohol (hereinafter abbreviated as PVA) is to have a degree of polymerization, that is, a viscosity average degree of polymerization (hereinafter abbreviated simply as degree of polymerization) in the range of 300 to 700. With a degree of polymerization less than 300, the strength of the male-type engaging elements of the obtained male-type molded hook-and-loop fastener decreases. On the other hand, with a degree of polymerization more than 700, the melt viscosity increases and the moldability is deteriorated to easily cause gelling so that a molten resin cannot reach the tips of cavities, and as a result, it is difficult to obtain a male-type molded hook-and-loop fastener having male-type engaging elements that extend to the tips. In particular, when the male-type engaging elements have a fine shape, the impact of the deterioration in moldability is significant. Preferably, the degree of polymerization is in the range of 350 to 600, and more preferably in the range of 370 to 550.

The degree of polymerization (viscosity average degree of polymerization) is a value obtained by measurement according to JIS K 6726:1994. Specifically, when the degree of saponification is less than 99.5% by mole, an intrinsic viscosity [η] (L/g) of a PVA saponified to a degree of saponification more than 99.5% by mole measured in water at 30° C. is used to determine the viscosity average degree of polymerization (P) according to the following formula.

$$P=([\eta]\times 104/8.29)(1/0.62)$$

The degree of saponification of PVA is to be in the range of 60 to 80% by mole. When the degree of saponification is less than 60% by mole, the fastener is too soft to achieve a strength and elastic modulus required for a male-type engaging element of a hook-and-loop fastener, thus not achieving an engaging force. Particularly when the male-type engaging elements have a fine shape, this trend is significant. On the other hand, when the degree of saponification is more than 80% by mole, the fastener is inferior in water solubility and thus cannot rapidly dissolve, and furthermore the moldability is deteriorated and gelling is liable to occur so that a molten resin cannot reach the tips of cavities, hardly providing a male-type molded hook-and-loop fastener having male-type engaging elements that extend to the tips. Particularly when the male-type engaging elements have a fine shape, gelling significantly occurs. The degree of saponification is preferably in the range of 70 to 80% by mole, and further preferably in the range of 72 to 78% by mole.

The degree of saponification is a value obtained by measurement according to JIS K6726:1994.

A method of producing such a PVA is not particularly limited, but in general, PVA is produced by hydrolysis or alcoholysis of polyvinyl acetate, and also in the present invention, the PVA is preferably a saponified product of a homopolymer of vinyl acetate. Of course, to the extent that the water solubility, moldability, and the like of the PVA are not largely impaired, a small amount of another vinyl monomer, for example, vinyl formate, vinyl acetate, vinyl propionate, vinyl versatate, vinyl pivalate, or the like, or another α-olefin or the like may be co-polymerized therewith, and one obtained by modifying a terminal of a polymer can also be used. Examples of a method of polymerizing polyvinyl acetate include solution polymerization, bulk polymerization, pearl polymerization, and emulsion polymerization.

Next, the polyhydric alcohol- or ethylene oxide-based polymer used as a raw material constituting the water-soluble male-type molded hook-and-loop fastener of the present invention will be described.

The polyhydric alcohol is a tri- or higher valent aliphatic alcohol, and examples thereof include glycerol, pentaerythritol, and sorbitol. An alkylene oxide, such as ethylene oxide or propylene oxide, may be added to the alcohol group. Among them, compounds in which 2 to 10 moles of ethylene oxide is added to glycerol and sorbitol are preferred because of the high plasticizing effect on PVA.

A specific examples of the ethylene oxide-based polymer is polyethylene glycol. Particularly in point of less causing bleeding out or in point of less vaporizing in formation of the hook-and-loop fastener, thus less causing deterioration of the work environment, a lower polymer polyethylene glycol having a number average molecular weight of 300 to 700 is most preferred among the polyhydric alcohol- or ethylene oxide-based polymers as described above.

Use of such a polyethylene glycol having a low number average molecular weight increases the moldability of PVA, and makes the obtained male-type molded hook-and-loop fastener flexible. On the other hand, when the number average molecular weight is 300 or more, the polyethylene glycol hardly bleeds out on the surface of the obtained male-type molded hook-and-loop fastener and the surface is hardly tackified. When the number average molecular weight is 700 or less, the moldability is more superior. The polyethylene glycol more preferably has a number average molecular weight in the range of 350 to 500, and particularly preferably in the range of 370 to 450.

A small amount of an alkylene oxide, for example, propylene oxide may be co-polymerized into the polyethylene glycol.

The number average molecular weight of a polyethylene glycol compound in the present invention is a value measured as follows. 1 g (weighed to the digit of 0.1 mg) of a polyethylene glycol sample to be measured is put in 25 mL of a phthalic anhydride pyridine solution accurately measured with a stoppered flask, and the flask with a stopper is heated in a boiled water bath for 2 hours, and is allowed to cool to room temperature. Then, 50 mL (accurately measured) of a 0.5 mol/L aqueous sodium hydroxide solution and 10 drops of a phenol phthalein solution for titration are put in the flask. The liquid in the flask was titrated with a 0.5 mol/L aqueous sodium hydroxide solution, a point at which the liquid has kept the red color for 15 seconds is taken as the end point. Based on the thus determined titer M (mL) in this test and a titer R (mL) determined by a blank test performed in the same manner except for using no polyethylene glycol sample, the number average molecular weight is calculated according to the formula: Number average molecular weight={(Weight of polyethylene glycol sample (g))×4000}/{(M−R)×0.5 (mol/L)}.

The amount of the polyhydric alcohol- or ethylene oxide-addition polymer (these compounds are sometimes representatively referred to as a polyethylene glycol compound) added is in the range of 5 to 30 parts by mass based on 100 parts by mass of the PVA. With an amount less than 5 parts by mass, the effects of addition of polyethylene glycol, that is, improvement in moldability and flexibility of a molded object, are not achieved, and with an amount more than 30 parts by mass, the polyethylene glycol bleeds out on a surface of the obtained male-type molded hook-and-loop fastener to tackify the surface, and furthermore, the male-type engaging elements of the obtained male-type molded hook-and-loop fastener do not have a sufficient strength. The amount is preferably in the range of 7 to 25 parts by mass, and particularly preferably in the range of 8 to 23 parts by mass.

In addition, a layered inorganic particle is added to raw materials constituting the water-soluble male-type molded hook-and-loop fastener of the present invention. The layered inorganic particle reduces the tackiness of a surface of the obtained male-type molded hook-and-loop fastener, and furthermore, layers are arranged in parallel to the resin flowing direction in molding, and thus an excellent strength and the like are provided to the obtained molded product without largely impairing the flowability of the molded liquid in spite of addition of a solid material.

In addition, when male-type engaging elements are produced by a method including press-filling a resin molten product into male-type engaging element-shaped cavities perforated in a metal roll surface, cooling and solidifying the molten product as it is, and then peeling the solidified product from the metal roll surface, the layer surfaces of the layered inorganic particle added to the molten resin are arranged in parallel to a molten resin flowing direction. As a result, breaking or tearing of a male-type engaging element in mid-course of a cavity and crack generation can be inhibited in pulling the cooled and solidified male-type engaging elements out of the cavities. Also when the male-type engaging elements of the obtained male-type hook-and-loop fastener are engaged with and peeled from loop-shaped engaging elements, breaking or tearing of the male-type engaging elements or the like can be inhibited. Furthermore, since layer surfaces of the layered inorganic particle are arranged in parallel to the surface of the molded product, bleeding out of the polyethylene glycol compound from the interior of the molded product to a molded product surface is easily inhibited. On the other hand, when the inorganic particle has a needle- or particle-shape, the bleeding out is not so easily inhibited as in the layered inorganic particle.

Specific examples of the layered inorganic particle include kaolin, halloysite, talc, pyrophyllite, smectite, vermiculite, and mica, and among them, talc is preferred. Talc is a pulverized product of a hydrated magnesium silicate, and functions to increase the moldability in molding the male-type molded hook-and-loop fastener, to increase the strength of the obtained male-type engaging elements, and further to make the surface of the obtained male-type molded hook-and-loop fastener non-tacky.

That is, the male-type molded hook-and-loop fastener of the present invention is produced by pulling male-type engaging elements from cavities in a die, and has features in that tearing of the male-type engaging elements in mid-course of the cavities can be prevented in pulling, and tearing of the molded male-type engaging elements can be prevented in use, and furthermore, tackifying of a surface of the obtained male-type molded hook-and-loop fastener is inhibited even under a high-humidity condition. The average particle diameter of the layered inorganic particle is preferably in the range of 0.1 to 100 μm, and particularly preferably in the range of 1 to 20 μm. The "average particle diameter" herein refers to the 50% particle diameter (D50), and can be measured with, for example, a particle size distribution analyzer (Nanotrac (registered tradename) particle size distribution analyzer UPA-EX150 manufactured by Nikkiso Co., Ltd.) in which a laser doppler method is applied.

The amount of the layered inorganic particle added is 3 to 20 parts by mass based on 100 parts by mass of the PVA. With an amount less than 3 parts by mass, the effect of addition of the layered inorganic particle as described above is not achieved, whereas with an amount more than 20 parts by mass, the flowability of the resin is deteriorated to impair the moldability. The amount is preferably in the range of 4 to 15 parts by mass and in the range of ⅓ to ⅔ of the amount of the polyethylene glycol compound added, and particularly preferably in the range of 5 to 12 parts by mass and in the range of ⅖ to ⅗ of the amount of the polyethylene glycol compound added.

The male-type molded hook-and-loop fastener of the present invention is constituted of the PVA, the polyethylene glycol compound, and the layered inorganic particle as described above, and besides the above components, other substances can be added to the extent that the moldability is not impaired and the strength, the water disintegrability, and the like of the obtained male-type molded hook-and-loop fastener are not impaired. For example, by incorporating a colorant, such as a pigment or a dye, the state of dissolution of the hook-and-loop fastener in water can be easily visually recognized. A reinforcing filling material can also be added.

The total amount of the PVA, the polyethylene glycol compound, and the layered inorganic particle in the materials constituting the male-type molded hook-and-loop fastener is preferably 80% by mass or more, more preferably 90% by mass, further preferably 95% by mass or more, for example, 100% by mass.

Next, a method of molding a male-type molded hook-and-loop fastener from such a PVA-based water-soluble resin mixture will be described. As a specific method of producing the water-soluble male-type molded hook-and-loop fastener of the present invention, a method including pouring a resin molded liquid in a sheet form onto a surface of a metal roll having a plurality of male-type engaging element-shaped cavities provided on the surface thereof while press-filling the molded liquid into the cavities, cooling and solidifying the molded liquid, and then peeling the solidified product from the metal roll surface while pulling the solidified product out of the cavities, thereby producing a sheet having a plurality of male-type engaging elements on the surface.

The production method including peeling from the cavities is specifically described in more detail. By alternately superposing ring-shaped dies each having a thickness of 0.2 to 0.5 mm and having carvings of a male-type engaging element-shape, such as an inverted J-shape or a Y-shape, engraved on the outer circumference and metal rings having no carvings engraved therein, a die roll having a plurality of cavities having carvings of the male-type engaging element-shape on the circumferential surface thereof is provided.

In the case of male-type engaging elements in which the direction to be engaged is one direction, such as an inverted J-shape, it is preferred that half of the ring-shaped dies having inverted J-shaped carvings are replaced with ring-shaped dies having a thickness of 0.2 to 0.5 mm and having engraved on the outer circumference carvings of an inverted J-shape that curves in the opposite direction to the inverted J-shape. In this case, the ring-shaped dies of the inverted J-shape that curves in the opposite direction and the ring-shaped dies of the inverted J-shape that curves in the original direction may be alternately disposed or may be disposed alternately every two or more dies.

On the surface of such a metal roll, a plurality of cavities that each curve in the roll circumferential direction are arranged in rows in the circumferential direction, and a plurality of such rows are present in parallel in the metal roll width direction. In the case of the inverted J-shape, the direction of curving of the cavities is reversed every row or every two or more rows. In this case, regardless of the inverted J-shape or the Y-shape, each of the cavities is tapered from the metal roll surface toward the tip portion, and gradually curves in mid-course in the metal roll circumferential direction so that the tip portion is oriented toward the metal roll surface.

In a specific method of pouring a molten resin onto the metal roll surface and molding the molten resin, a resin molten product is ejected into a gap between the metal roll and another drum roll disposed at a position facing the metal roll and is pressed to thereby press-fill the molten product into the cavities and at the same time, a sheet having a uniform thickness is formed on the roll surface, and while the die roll rotates, the molten product in the cavities is cooled and solidified with a refrigerant continuously circulated in the roll and at the same time, the molten product is extended with a gap-adjusted nip roller so that a substrate of the resulting male-type molded hook-and-loop fastener has a uniform thickness, and the cooled sheet is peeled from the die roll surface while pulling male-type engaging elements out of the cavities. Thus, a sheet-shaped object having a plurality of male-type engaging elements on the surface, that is, a male-type molded hook-and-loop fastener is obtained.

The water-soluble male-type molded hook-and-loop fastener of the present invention obtained in such a method has a plurality of male-type engaging elements arranged in rows, and each of the engaging elements has a shape in which the element rises from the substrate surface, curves, in mid-course, in the row direction so that a tip portion thereof is oriented toward the substrate surface (inverted J-shape), or each of the engaging elements has a shape in which the element rises from the substrate surface, branches in mid-course forward and backward in the row direction so as to curve in the row direction so that each branched tip portion is oriented toward the substrate surface (Y-shape).

By having such a shape, the male-type engaging elements hardly fall over by a pressure from above, and the plurality of male-type engaging elements cooperatively resist a pulling force in the engaging element-row direction by loop-shaped engaging elements to be engaged. Thus, a high engaging force can be achieved.

In the present invention, the male-type engaging elements may rise directly from the substrate surface, or may rise from furrow-shaped enlarged portions formed on the substrate surface. When the male-type engaging elements thus rise from furrow-shaped enlarged portions, the rate of dissolution in water is increased, which is preferred. The height of the furrow-shaped enlarged portions is preferably in the range of 1/20 to 1/3 of the substrate thickness from the substrate surface. Examples of a method for allowing the male-type engaging elements to rise from furrow-shaped enlarged portions include a method in which the diameter of the ring-shaped die with cavities is made slightly smaller than the diameter of the adjacent ring-shaped die with no cavities, and a method in which the center of the ring-shaped die with cavities is shifted from the center of the adjacent ring-shaped die. Not all the male-type engaging elements are to rise from furrow-shaped enlarged portions, and a certain effect is achieved even in the case of a part thereof.

Figure 1:
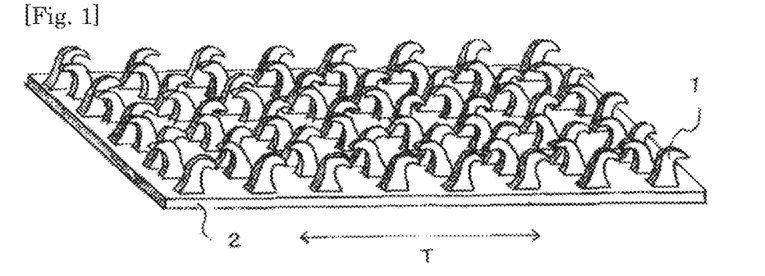
FIG. 1 is a perspective view of an example of the water-soluble male-type molded hook-and-loop fastener of the present invention.
Figure 2:
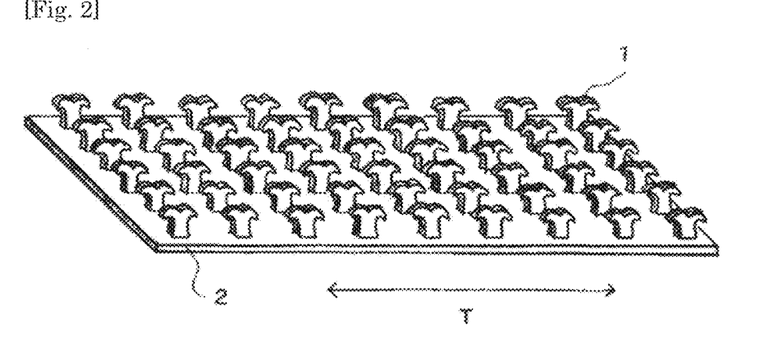
FIG. 2 is a perspective view of another example of the water-soluble male-type molded hook-and-loop fastener of the present invention.

In the male-type molded hook-and-loop fastener shown in FIG. 1, a plurality of male-type engaging elements (1) are arranged in rows, and each of the engaging elements has a shape in which the element rises from a surface of a substrate (2), and curves, in mid-course, in a row direction (T) so that a tip portion thereof is oriented toward the substrate surface (inverted J-shape). In the male-type molded hook-and-loop fastener shown in FIG. 2, a plurality of male-type engaging elements (1) are arranged in rows, and each of the engaging elements has a shape in which the element rises from a surface of a substrate (2), and branches in mid-course forward and backward in a row direction (T) so as to curve in the row direction so that each branched tip portion is oriented toward the substrate surface (Y-shape).

In particular, in the present invention, when the male-type engaging elements each have a shape in which the element rises from a surface of the substrate, curves, in mid-course, in the row direction so that a tip portion thereof is oriented toward the substrate surface (inverted J-shape), the height of each male-type engaging element from the substrate surface to the top of the male-type engaging element is preferably 1.2 mm or less, and when the male-type engaging elements each have a shape in which the element branches in mid-course forward and backward in the row direction so as to curve in the row direction so that each branched tip portion is oriented toward the substrate surface (Y-shape), the height of each male-type engaging element from the substrate surface to the top of the male-type engaging element is preferably 0.6 mm or less.

In general, a male-type engaging element of a male-type molded hook-and-loop fastener has a height of 1.5 mm or more in many cases, and generally has a height of about 2 to 3 mm. However, in the present invention, the height is preferably 1.2 mm or less or 0.6 mm or less which is lower than such a conventionally common height in terms of water solubility and further in terms of the application.

When the height of the male-type engaging element is low, in conjunction with the flexibility of the male-type engaging element, the foreign-body sensation can be suppressed and rough skin is not hardly caused in contact with the skin even in attachment to a part that often comes in contact with the skin, such as a sanitary good, and in addition, the time required for dissolution can be reduced more.

The lower limit of the height of the male-type engaging element is not particularly limited, but is, for example, 0.1 mm, may be 0.2 mm, or may be 0.4 mm. When the male-type engaging element has an inverted J-shape, the lower limit of the height of the male-type engaging element is, for example, 0.4, may be 0.6, or may be 0.8 mm.

Such short male-type engaging elements can be obtained by using a metal roll in which cavities are not deeply engraved from the metal roll surface. Specifically, when producing male-type engaging elements each having a shape in which the element rises from a surface of the substrate, curves, in mid-course, in the row direction so that a tip portion thereof is oriented toward the substrate surface (inverted J-shape), a metal roll in which the cavities have a largest depth from the metal roll surface of 1.2 mm or less is used, and when producing male-type engaging elements each having a shape in which the element branches in mid-course forward and backward in the row direction so as to curve in the row direction so that each branched tip portion is oriented toward the substrate surface (Y-shape), a metal roll in which the cavities have a largest depth from the metal roll surface of 0.6 mm or less is used. Thus, such mole type engaging elements can be easily obtained.

In the water-soluble male-type molded hook-and-loop fastener of the present invention, the thickness of the substrate layer is preferably in the range of 0.15 to 0.3 mm in terms of rapid water disintegrability and the strength of the hook-and-loop fastener. In the water-soluble male-type molded hook-and-loop fastener of the present invention, the element density of the male-type engaging element is preferably 60 to 160/cm$^2$.

The water-soluble male-type molded hook-and-loop fastener of the present invention may be a double-sided hook-and-loop fastener having male-type engaging elements on both the front and back surfaces obtained by bonding, on the back surface of a water-soluble male-type molded hook-and-loop fastener, a similar water-soluble male-type molded hook-and-loop fastener, for example, by thermal press or by a water-soluble adhesive, or may be a double-sided hook-and-loop fastener having male-type engaging elements on both the front and back surfaces obtained by using a metal roll having cavities on the surface also as the metal roll for the back surface side so that male-type engaging elements are present also on the back surface side in molding so that male-type engaging elements are present also on the back surface. Alternatively, a water-disintegrable nonwoven fabric or the like having loop fibers on the surface thereof may be integrated on the back surface side in the same manner, thus providing a water-soluble hook-and-loop fastener that has male-type engaging elements on the front surface and has loop-shaped engaging elements on the back surface.

The thus obtained water-soluble male-type molded hook-and-loop fastener of the present invention has such a water solubility as to completely dissolve in water of 25° C. within 20 minutes. In addition, in the water-soluble male-type molded hook-and-loop fastener of the present invention, 98% or more of the male-type engaging elements present in the surface preferably each have a tip portion that is oriented toward the substrate surface without ending in mid-course.

The water-soluble male-type molded hook-and-loop fastener of the present invention, when comes in contact with water, dissolves to lose the engaging ability, and furthermore, the water-soluble male-type molded hook-and-loop fastener itself completely dissolves and disappears. Accordingly, a loop-type hook-and-loop fastener to be engaged is not required to be water soluble, but when the fastener to be engaged is water soluble as required, it is possible to allow the presence of the entire hook-and-loop fastener itself to disappear.

An example of a water-soluble loop-type hook-and-loop fastener used to be engaged is one made of a water-soluble fiber that can dissolve in normal temperature water, and in particular, as a water-soluble fiber, a PVA-based fiber is preferred since it has a superior tensile strength and it is superior in handleability. Examples thereof include a water-soluble PVA-based fiber (Kuralon K-II (registered tradename) WN2) obtained by subjecting, to dry-wet spinning or wet spinning in a methanol bath, a spinning dope in which a PVA having a degree of saponification of 85 to 90% by mole and a degree of polymerization of 1500 to 2000 available from Kuraray Co., Ltd. is dissolved in dimethyl sulfoxide, a water-soluble PVA-based fiber obtained by blending a polyethylene glycol or a sorbitol ethylene oxide adduct with a PVA having a degree of saponification of 60 to 80% by mole and a degree of polymerization of 300 to 700 and subjecting the mixture to melt spinning, or a water-soluble PVA-based fiber obtained by subjecting a spinning dope in which a PVA having a degree of saponification of 85 to 95% by mole is dissolved in water to wet spinning in a saturated aqueous sodium sulfate solution bath.

An example of a loop-type hook-and-loop fastener made of such a water-soluble fiber is a nonwoven fabric or woven or knitted fabric made of such a water-soluble fiber having loops made of the same water-soluble fiber on a surface thereof.

A specific example in the case of a nonwoven fabric is a nonwoven fabric in which loops made of a water-soluble fiber are provided on the surface, obtained by forming the water-soluble fiber into a web, entangling the web with a needle punch or the like, and raising the surface thereof as needed.

Examples in the case of a woven or knitted fabric include a woven fabric-type loop-type hook-and-loop fastener in which a water-soluble fiber is used as a spun yarn and the spun yarn is used as warp and weft to fabricate a woven fabric, and the spun yarn is further woven therein in parallel to the warp while providing some loops protruding on the woven fabric surface, and a knitted fabric-type loop-type hook-and-loop fastener in which a spun yarn made of such a water-soluble fiber is used to fabricate a knitted fabric, and the knitted fabric surface is raised using a card clothing or the like to provide loops made of the water-soluble fiber on the woven fabric surface. In the case where the water-soluble fiber is a multifilament yarn, the multifilament yarn is used as warp and weft to fabricate a woven fabric, and a multifilament yarn for loop-shaped engaging element is woven therein in parallel to the warp while providing some loops protruding on the woven fabric surface.

The woven or knitted fabric may be one in which such a water-soluble multifilament yarn is formed into a nonwoven fabric by a spunbonding method, and the surface is raised to provide loops made of a water-soluble fiber protruding on the surface.

In the case of a loop-type hook-and-loop fastener, it is preferred that the back surface or a part of the back surface is thermally pressed to fix fibers so that the loop-shaped engaging elements cannot be pulled out from the substrate fabric.

A loop-type hook-and-loop fastener made of a water-soluble fiber which dissolves in normal temperature water has problems as follows: a normal temperature water-soluble fiber constituting the loop-shaped engaging elements gets tackiness in a high humidity condition; loop-shaped engaging elements do not rise from the substrate fabric surface but fall over thereon and thus cannot sufficiently engage with male-type engaging elements, or even if can engage therewith, the loop-shaped engaging elements are easily cut, failing to provide a hook-and-loop fastener having a high engaging force; and the fiber that can dissolve in normal temperature water is required to be managed and stored so that it is not subjected to a high humidity condition and so that it is not brought in contact with moisture in the production process, storage process, and distribution process of the loop-type hook-and-loop fastener and further in use by consumers who buy the loop-type hook-and-loop fastener.

An example of a water-soluble loop-type hook-and-loop fastener released from such problems is a loop-type hook-and-loop fastener made of a water-soluble fiber that does not dissolve in normal temperature water but dissolves only after coming in contact with hot water of 50 to 80° C. Such a water-soluble loop-type hook-and-loop fastener is not a normal temperature water-soluble one, but dissolves in hot water used in recovering and regenerating disposable products having a hook-and-loop fastener attached, and thus has a high utility value from an environmental standpoint.

A specific example of such a loop-type hook-and-loop fastener that dissolves in hot water is a water-soluble loop-type hook-and-loop fastener which includes a substrate fabric made of a water-soluble PVA-based fiber having a water dissolution temperature of 50 to 80° C. and loop-shaped engaging elements made of the same fiber rising from a surface of the substrate. Preferred examples thereof include: a loop-type hook-and-loop fastener in which many loop-shaped engaging elements including loops made of a water-soluble PVA fiber are provided on a surface of a woven or knitted fabric or a nonwoven fabric made of the same water-soluble PVA fiber, the water-soluble PVA fiber being obtained by subjecting a spinning dope in which a PVA having a degree of saponification of 90 to 97% by mole and a degree of polymerization of 1200 to 2000 is dissolved in dimethyl sulfoxide as described above to wet spinning or dry-wet spinning in methanol; a tricot knitted fabric in which many loops made of a multifilament yarn are provided on a surface of a tricot knitted fabric made of a multifilament yarn, the multifilament yarn being obtained by blending, as described above, a polyethylene glycol or a sorbitol ethylene oxide adduct with a PVA-based resin that has a degree of saponification of 90 to 97% by mole and a degree of polymerization 250 to 500, preferably 300 to 450, further preferably 350 to 400 and that has 5 to 10% by mole, preferably 6.5 to 9.5% by mole, and further preferably 7.5 to 9.2% by mole of ethylene co-polymerized therein, subjecting the blend to melt spinning. In particular, the tricot knitted fabric is preferred in terms of the engaging force.

Furthermore, in the case of the water-soluble hook-and-loop fastener as described above in which two fasteners are bonded to each other so that the male-type elements are present on the front surface and the loop-shaped elements are present on the back surface, where the two fasteners are bonded so that the male-type engaging elements are present on the front surface and the loop-shaped engaging elements are present on a place of the back surface that is apart from the place where the male-type engaging elements are present, the tricot knitted fabric as described above is preferably used as the water-soluble loop-type hook-and-loop fastener since such a water-soluble loop-type hook-and-loop fastener is required to have a sufficient tensile strength by itself.

Then, a loop-type hook-and-loop fastener made of such a water-soluble fiber having a water dissolution temperature of 70 to 90° C. does not dissolve in normal temperature water but can easily dissolve in hot water, and even when it is discarded, it is decomposed in a short time, and thus is also environmentally friendly.

The water-soluble male-type molded hook-and-loop fastener obtained by the present invention has a sufficient engaging force, and rapidly dissolves in normal temperature water, and contains no substance that inflicts harm on the human body. Accordingly, the water-soluble male-type molded hook-and-loop fastener can be used alone or as a combination with a water-soluble female-type hook-and-loop fastener, as a fixing material for fixing a sanitary good on underwear, as a fixing material of a lumbar part of a disposable diaper, or as a fixing material for other disposable goods.

In addition, the fastener can be used in an application in which, for example, by throwing an article having the fixed hook-and-loop fastener in water, the fixation by the hook-and-loop fastener is immediately lost to expand the article in water or on a water surface. For example, the fastener can be used for fixing or binding an oil fence, a shielding sheet, etc. in nonuse which is used as a shield for preventing oil or polluted water from diffusing or flowing from a tanker, facility, etc. into a sea surface, river, or the like. In the case of a water-soluble hook-and-loop fastener having male-type engaging elements on the front surface and female-type engaging elements on the back surface, the fastener can also be used as a self-engaging water-soluble binding tape, fixing belt, or the like in which binding is released when the fastener is wetted.

Such a water-soluble hook-and-loop fastener (hereinafter abbreviated as water-soluble loop-type hook-and-loop fastener) that has male-type engaging elements on the front surface and female-type engaging elements (hereinafter abbreviated as loop-shaped engaging elements) on the back surface may be obtained by superposing a water-soluble male-type molded hook-and-loop fastener and a water-soluble loop-type hook-and-loop fastener back to back so that the engaging elements are present on the respective outer surfaces, and bonding the two fasteners at some points with a water-soluble adhesive or by thermal press. Alternatively, the above water-soluble hook-and-loop fastener may be obtained by: superposing on an end portion of a water-soluble male-type molded hook-and-loop fastener having male-type engaging elements on the front surface, an end portion of water-soluble loop-type hook-and-loop fastener having loop-shaped engaging elements on the back surface so that the parts other than the end portions do not overlap and so that the face having the male-type engaging elements is on the front side and the face having the loop-shaped engaging elements is on the back side; and bonding the overlapping parts of the two fasteners with a water-soluble adhesive or by thermal press so that the male-type engaging elements are present on the front surface and the loop-shaped engaging elements are present on a place of the back surface that is apart from the place where the male-type engaging elements are present (that is, the place where the male-type engaging elements are present and the place where the loop-shaped engaging elements are present are not bonded back to back but extend to the directions apart from each other from the bonded place).

EXAMPLES

The present invention will be described below with reference to examples. In examples, the engaging force was measured as follows. E40000 (manufactured by Kuraray Fastening Co., Ltd.) was used as a loop-type hook-and-loop fastener to be engaged and the initial engaging force and the engaging force after repeating engaging and peeling 10 times were measured according to JIS L3416:2000.

The water disintegrability of the obtained water-soluble male-type molded hook-and-loop fastener was measured as follows. 100 cc of water of a temperature of 25° C. was put in a 200 mL beaker, 0.025 g of the water-soluble male-type molded hook-and-loop fastener was placed in this water, and the time taken for completely dissolving the fastener with stirring (using a magnet stirrer with a stirring bar of 12 mm length at a speed of 1500 rpm/min) was measured.

The shape completeness of the male-type engaging elements of the obtained water-soluble male-type molded hook-and-loop fastener was determined as follows. Among arbitrary selected 100 male-type engaging elements of the water-soluble male-type molded hook-and-loop fastener, the number of engaging elements that did not have a tip portion oriented toward the substrate surface but ended in mid-course was counted.

The flexibility of the obtained water-soluble male-type molded hook-and-loop fastener was determined as follows. A man of 60 kg body weight threaded on the hook-and-loop fastener 10 times with a bare foot, and then the state and the like of the engaging elements was observed.

The presence or absence of surface tackiness was determined as follows. The obtained hook-and-loop fastener was left in a condition at a temperature of 30° C. and a humidity of 100% for 4 hours and then a surface of the hook-and-loop fastener was touched and the presence or absence was determined by the sense of touch.

Example 1

As dies, a ring-shaped die of 0.30 mm thickness and 212 mm diameter having shapes of hook-shaped engaging element (inverted J-shaped engaging element) with 0.90 mm depth engraved on the outer circumference, and a metal ring of 0.30 mm thickness and 212 mm diameter having no such engraved shapes, a ring-shaped die of 0.30 mm thickness and 212 mm diameter having hook-shaped engaging element-shapes oriented in the opposite direction to the above hook-shaped engaging element-shapes engraved on the outer circumference, and a metal ring of 0.30 mm thickness and 212 mm diameter having no such engraved shapes were sequentially superposed to provide a die roll with 120 mm width having on the circumferential surface a plurality of cavities each having an inverted J-shaped engaging element-shape and a plurality of cavities each having an engaging element-shape oriented in the opposite direction thereto. The diameter of the ring-shaped die having hook-shaped engaging element-shapes engraved on the outer circumference was slightly smaller than the diameter of the rings adjacent thereto on the both sides (so that furrow-shaped enlarged portions with 0.03 mm height were formed as described later).

20 parts by mass of a polyethylene glycol having a number average molecular weight of 400 and 10 parts by mass of talc (average particle diameter: 4 μm) were mixed with 100 parts by mass of a PVA obtained by saponifying a vinyl acetate having a degree of polymerization of 500 into a degree of saponification of 74% by mole were mixed to prepare a composition. The composition was molten at 190° C. to produce a molten product. The molten product was ejected into a gap between the above die roll and another drum roll disposed at a position facing the die roll, and was pressed with the die roll and the drum roll, whereby the resin composition was filled in the cavities while forming a sheet having a uniform thickness on the roll surface. While the die roll rotated, the resin composition in the cavities was cooled with water continuously circulated in the roll, and then, the product was extended with a gap-adjusted nip roller so as to provide a substrate thickness of 0.20 mm while the cooled and solidified sheet was peeled from the die roll surface, thereby producing a water-soluble male-type molded hook-and-loop fastener.

In the obtained water-soluble male-type molded hook-and-loop fastener, a plurality of male-type engaging elements were arranged in rows, and each of the male-type engaging elements had a shape in which the element rose from a furrow-shaped enlarged portion (height 0.03 mm) formed on the substrate surface, curved in mid-course in the row direction so that a tip portion thereof was oriented toward the substrate surface (inverted J-shape). The height thereof was 0.94 mm, the element density was 110/cm$^2$, and the thickness of the substrate was 0.21 mm.

The performance of the obtained water-soluble male-type molded hook-and-loop fastener is shown in Table 1. As is apparent from this table, the obtained fastener had almost no problem about all the water solubility, the engaging force, the state of engaging elements on the surface, the flexibility, and the surface tackiness, was suitable as an attaching material of a sanitary good onto underwear, and was considered to arise no problem even if thrown into toilet after use.

Furthermore, as a fastener to be engaged with the water-soluble male-type molded hook-and-loop fastener, a nonwoven fabric with a basis weight of 200 g/m$^2$ having loops made of the same fiber as for the nonwoven fabric on the surface thereof was used and engaged. The nonwoven fabric was obtained by forming a web of a water-soluble PVA fiber (Kuralon K-IIWN2, thickness: 2.2 dtex, fiber length: 51 mm) manufactured by Kuraray Co., Ltd. which is soluble in normal temperature water, and entangling the web with a needle punch, and further raising the surface with a card clothing. The engaging force was as high as a level which was slightly less than the value shown in Table 1, and thus the engaging ability was superior. The water-soluble male-type molded hook-and-loop fastener and the nonwoven fabric made of the water-soluble fiber which were engaged with each other were cut into a 2 cm square, and were dipped in water of a normal temperature at 25° C. with stirring, and the state of dissolution was observed. Then, the engagement of the hook-and-loop fasteners was released in 3 minutes, and both the fasteners were completely dissolved in 15 minutes. Furthermore, as a fastener to be engaged with the water-soluble male-type molded hook-and-loop fastener, a loop-type hook-and-loop fastener having a basis weight of 145 g/m$^2$ and a loop height of 1.1 mm made of a tricot knitted fabric with a course of 75c/inch and a wale of 28 w/inch was used and was engaged. The tricot knitted fabric was made of a water-soluble PVA-based fiber (Mintval CR-700P RS41T-6, a multifilament yarn of bundled 12 filaments each of 8.5 dtex thickness, obtained by melt spinning a resin, the resin being obtained by blending 8 parts of a 2-mol % ethylene oxide adduct of sorbitol with 100 parts of a PVA, the PVA having a degree of polymerization of 390 and a degree of saponification of 95% by mole and having 8.5% by mole of ethylene co-polymerized therein) manufactured by Kuraray Co., Ltd. which was soluble in water of 80° C.

This loop-type hook-and-loop fastener had a higher proportion of loop-shaped engaging elements that did not fall over but rose from the substrate fabric surface than the nonwoven fabric described above, and the engaging force was higher than that of the above nonwoven fabric. This fastener did not dissolve in normal temperature water of 25° C., but completely dissolved in hot water of 80° C. in 10 minutes, and when buried in soil, it completely disappeared in 24 weeks. As compared with the water-soluble nonwoven fabric described above, for this water-soluble tricot knitted fabric, it was less required to manage the humidity in production and storage, and this tricot knitted fabric was able to be handled in the same manner as a general synthetic fiber.

TABLE 1

|  | Water solubility (sec) | Engaging force | | State of engaging elements on surface | Flexibility | Surface tackiness |
|  |  | Initial value | After engaging and peeling 10 times |  |  |  |
| --- | --- | --- | --- | --- | --- | --- |
| Example 1 | 850 | shear: 18.4 peel: 1.26 | shear: 18.1 peel: 1.22 | 99% with tip portion | breakage not observed | none | shear: N/cm$^2$,
peel: N/cm

Examples 2 to 5, Comparative Examples 1 to 4

Water-soluble male-type molded hook-and-loop fasteners were produced in the same manner as in Example 1 except for changing the PVA used in Example 1 to a PVA having a degree of polymerization and a degree of saponification shown in Table 2. In all the obtained water-soluble male-type molded hook-and-loop fasteners, as with the case of Example 1, a plurality of male-type engaging elements were arranged in rows, and each of the engaging elements had a shape in which the element rose from the substrate surface, curved in mid-course in the row direction so that a tip portion thereof was oriented toward the substrate surface (inverted J-shape). The height of the male-type engaging element was 0.94 mm, the element density was 110/cm², and the thickness of the substrate was 0.25 m.

TABLE 2

|  | Degree of polymerization of PVA | Degree of saponification of PVA (% by mole) |
|---|---|---|
| Example 2 | 350 | 74 |
| Example 3 | 650 | 75 |
| Comparative Example 1 | 250 | 74 |
| Comparative Example 2 | 1000 | 76 |
| Example 4 | 500 | 68 |
| Example 5 | 500 | 78 |
| Comparative Example 3 | 500 | 52 |
| Comparative Example 4 | 500 | 94 |

The performance of the obtained eight water-soluble male-type molded hook-and-loop fasteners is shown in Table 3. As is apparent from this table, the water-soluble male-type molded hook-and-loop fasteners of Examples 2 to 5 all did not have a large problem about all the engaging force, the state of engaging elements on the surface, the flexibility, and the surface tackiness, was usable as an attaching material of a sanitary good onto underwear as a specific application, and also regarding the water solubility, was considered to arise no problem even if thrown into toilet after use.

In contrast, in the case of a PVA having a lower degree of polymerization of Comparative Example 1, the male-type engaging elements had a low strength, and was easily broken. In the case of a PVA having a high degree of polymerization of Comparative Example 2, the melt viscosity was high and gelling occurred in the die so that the molten resin was not able to reach the tips of the cavities, about 20% of the male-type engaging elements did not extend to the tips, and the fastener was also inferior in the water solubility.

The fastener of Comparative Example 3 was too soft so that required levels of the strength and elastic modulus for male-type engaging elements of a hook-and-loop fastener was not achieved, and had a low engaging force. The fastener of Comparative Example 4 was inferior in the water solubility, and the moldability was also reduced to easily cause gelling so that the molten resin was not able to reach the tips of the cavities, and about 15% of the male-type engaging elements did not extend to the tips.

TABLE 3

|  | Water solubility (sec) | Engaging force | | State of engaging elements on surface | Flexibility | Surface tackiness |
|---|---|---|---|---|---|---|
|  |  | Initial value | After engaging and peeling 10 times |  |  |  |
| Example 2 | 600 | shear: 18.1 peel: 1.18 | shear: 17.8 peel: 1.15 | 99% with tip portion | breakage not observed | none |
| Example 3 | 950 | shear: 19.1 peel: 1.31 | shear: 18.8 peel: 1.28 | 99% with tip portion | breakage not observed | none |
| Comparative Example 1 | 530 | shear: 5.0 peel: 0.3 | shear: 2.3 peel: 0.15 | 80% with tip portion | element molding failure, many breakages | none |
| Comparative Example 2 | ≥1800 | shear: 14.4 peel: 0.94 | shear: 14.2 peel: 0.92 | 82% with tip portion | element molding failure, many breakages | none |
| Example 4 | 830 | shear: 17.9 peel: 1.18 | shear: 17.6 peel: 1.16 | 99% with tip portion | breakage not observed | none |
| Example 5 | 980 | shear: 18.5 peel: 1.28 | shear: 18.2 peel: 1.25 | 99% with tip portion | breakage not observed | none |
| Comparative Example 3 | 550 | shear: 7.2 peel: 0.98 | shear: 3.5 peel: 0.3 | 85% with tip portion | element molding failure, many breakages | none |
| Comparative Example 4 | ≥800 | shear: 16.7 peel: 1.08 | shear: 13.9 peel: 1.06 | 85% with tip portion | element molding failure, many breakages | none | shear: N/cm²,
peel: N/cm

Examples 6 to 7, Comparative Examples 5 to 9

Water-soluble male-type molded hook-and-loop fasteners were produced in the same manner as in Example 1 except for changing the proportions of the PVA, polyethylene glycol, and talc used in molding in Example 1 to the values shown in Table 4.

In all the obtained water-soluble male-type molded hook-and-loop fasteners, as with the case of Example 1, a plurality of male-type engaging elements were arranged in rows, each of the engaging elements had a shape in which the element rose from the substrate surface, curved in mid-course in the row direction so that a tip portion thereof was oriented toward the substrate surface (inverted J-shape). The height of the male-type engaging element was 0.94 mm, the element density was 110/cm$^2$, and the thickness of the substrate was 0.25 m.

TABLE 4

|  | PVA (parts by mass) | PEG* (parts by mass) | Talc (parts by mass) |
|---|---|---|---|
| Example 6 | 100 | 10 | 5 |
| Example 7 | 100 | 25 | 15 |
| Comparative Example 5 | 100 | 40 | 25 |
| Comparative Example 6 | 100 | 3 | 2 |
| Comparative Example 7 | 100 | 0 | 10 |
| Comparative Example 8 | 100 | 20 | 0 |
| Comparative Example 9 | 100 | 0 | 0 |

PEG*: abbreviation of polyethylene glycol

The performance of the obtained seven water-soluble male-type molded hook-and-loop fasteners is shown in Table 5. As is apparent from this table, the water-soluble male-type molded hook-and-loop fasteners of Examples 6 and 7 were slightly inferior in any of the water solubility, the engaging force, the state of engaging elements on the surface, the flexibility, and the surface tackiness to the fastener of Example 1, but the levels were not so considerable, and the obtained fasteners were usable as an attaching material of a sanitary good onto underwear as a specific application, and were considered to arise no problem even if thrown into toilet after use.

In contrast, the water-soluble male-type molded hook-and-loop fastener of Comparative Example 5 in which the amounts of the polyethylene glycol and talc blended were both large was inferior in the moldability so that many male-type engaging elements were cut in mid-course in pulling out of the cavities. In addition, the polyethylene glycol bled out on the surface, and in spite of the large amount of talc added, the surface was tacky, and the male-type engaging elements of the obtained male-type molded hook-and-loop fastener did also not have a sufficient strength.

On the other hand, in Comparative Example 6 in which the amount of the polyethylene glycol and talc blended were both rather small, in Comparative Example 7 in which no polyethylene glycol was added, and in Comparative Example 9 in which no polyethylene glycol and no talc were added, gelling occurred during molding, and a male-type molded hook-and-loop fastener that was acceptable as a commercial product was not able to be produced, and particularly in Comparative Examples 7 and 9, even molding of the hook-and-loop fastener was not able to be performed.

In contrast, in Comparative Example 8 in which no talc was added, although the moldability was poor, a male-type molded hook-and-loop fastener was able to be produced. However, the obtained male-type molded hook-and-loop fastener had some male-type engaging elements that broke in mid-course, and the surface was very tacky so that the fastener was never acceptable as a commercial product.

TABLE 5

|  |  | Engaging force | | | | |
|---|---|---|---|---|---|---|
|  | Water solubility (sec) | Initial value | After engaging and peeling 10 times | State of engaging elements on surface | Flexibility | Surface tackiness |
| Example 6 | 930 | shear: 19.0 peel: 1.84 | shear: 18.7 peel: 1.32 | 99% with tip portion | breakage not observed | none |
| Example 7 | 880 | shear: 18.5 peel: 1.26 | shear: 18.3 peel: 1.23 | 99% with tip portion | breakage not observed | none |
| Comparative Example 5 | 800 | shear: 17.3 peel: 1.12 | shear: 16.0 peel: 1.02 | 87% with tip portion | with some-breakages | presence, not acceptable for practical use |
| Comparative Example 6 | 980 | shear: 5.2 peel: 0.33 | shear: 2.6 peel: 0.18 | 75% with tip portion | element molding failure, many breakages | none |
| Comparative Example 7 | — | — | — | not moldable | sheet broken | — |
| Comparative Example 8 | 850 | shear: 17.1 peel: 1.10 | shear: 16.8 peel: 1.07 | 90% with tip portion | considerably many breakages | presence, not acceptable for practical use |
| Comparative Example 9 |  |  |  | not moldable | sheet broken | — | shear: N/cm$^2$,
peel: N/cm

Example 8

Figure 3:
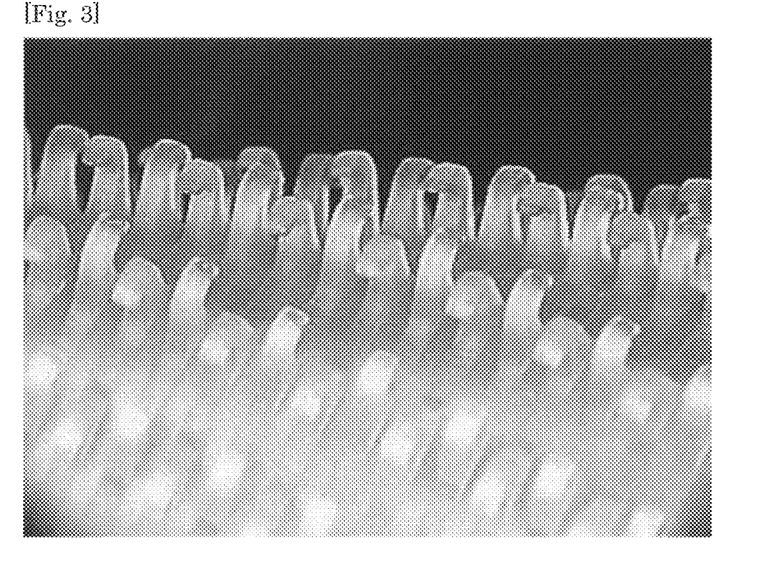
FIG. 3 is a drawing-substituted photograph showing a surface of an example of the water-soluble male-type molded hook-and-loop fastener of the present invention.

A water-soluble male-type molded hook-and-loop fastener was produced using the same resin mixture as in Example 1 in the same manner as in Example 1 except for using as the die roll for molding, a ring-shaped die of 0.3 mm thickness having a depth of each cavity engraved in the surface thereof of 1.2 mm. The obtained water-soluble male-type molded hook-and-loop fastener had male-type engaging elements having a height of 1.26 mm at an element density of 136/cm$^2$. The surface of the hook-and-loop fastener was as shown in FIG. 3, that is, had a plurality of male-type engaging elements, the plurality of male-type engaging elements being arranged in rows, each of the engaging elements having a shape in which the element rose from the substrate surface, curved in mid-course in the row direction so that a tip portion thereof was oriented toward the substrate surface (inverted J-shape). The thickness of the substrate was 0.23 mm. The performance of the obtained water-soluble male-type molded hook-and-loop fastener is shown in Table 6.

As is apparent from this table, the obtained fastener was somewhat inferior in the water solubility to that of Example 1, but had no problem in all the engaging force, the state of engaging elements on the surface, the flexibility, and the surface tackiness. However, the fastener was somewhat poor in the texture for an application in which the fastener is in contact with the skin, such as an attaching material of a sanitary good or the like to underwear. Regarding the point of throwing in toilet after use, there was a defect in that the dissolution time was slightly longer.

Example 9

A water-soluble male-type molded hook-and-loop fastener was produced using the same resin mixture as in Example 1 in the same manner as in Example 1 except for using a ring-shaped die of 0.3 mm thickness having engraved on the outer circumference carvings having a Y-shape having a depth of 0.55 mm as a shape of cavities in a die roll for molding. In the obtained water-soluble male-type molded hook-and-loop fastener, the male-type engaging elements on the surface were arranged in rows, and each of the engaging elements had a shape in which the element rose from the substrate surface, branched in mid-course forward and backward in the row direction so as to curve in the row direction so that each branched tip portion was oriented toward the substrate surface, that is, a Y-shape. The height thereof was 0.55 mm, the element density was 147/cm$^2$, and the thickness of the substrate was 0.18 mm. The performance of the obtained water-soluble male-type molded hook-and-loop fastener is shown in Table 6.

As is apparent from this table, the obtained fastener had a superior water solubility, engaging force, state of engaging elements on the surface, and flexibility which were at equal levels to those in Example 1, and the surface tackiness was not sensed as with the case of Example 1. The fastener was thus superior in usability. Furthermore, also regarding an application in which the fastener is in contact with the skin, such as an attaching material of a sanitary good or the like to underwear, the fastener was gentle on the skin and was superior in the texture, and was also able to rapidly dissolve when thrown in toilet after use. Thus, the fastener was excellent one with no problem.

TABLE 6

| | Water solubility (sec) | Engaging force Initial value | Engaging force After engaging and peeling 10 times | State of engaging elements on surface | Flexibility | Surface tackiness |
|---|---|---|---|---|---|---|
| Example 8 | 920 | shear: 17.8 peel: 0.51 | shear: 17.6 peel: 0.48 | 99% with tip portion | breakage not observed | none |
| Example 9 | 850 | shear: 16.9 peel: 0.43 | shear: 15.7 peel: 0.41 | 99% with tip portion | breakage not observed | none | shear: N/cm$^2$,
peel: N/cm

REFERENCE SIGNS LIST

1: Male-type engaging element
2: Substrate
T: Row direction of male-type engaging elements

The invention claimed is:

1. A water-soluble male-type molded hook-and-loop fastener, comprising:
   a substrate, and
   a plurality of male-type engaging elements protruding from a surface of the substrate,
   wherein the water-soluble male-type molded hook-and-loop fastener satisfies the following (1) to (3):
   (1) the plurality of male-type engaging elements are arranged in rows, and each of the male-type engaging elements has a shape in which the male-type engaging element rises from the substrate surface, curves in mid-course, in a row direction so that a tip portion thereof is oriented toward the substrate surface, or each of the male-type engaging elements has a shape in which the male-type engaging element rises from the substrate surface, branches in mid-course forward and backward in the row direction so as to curve in the row direction so that each branched tip portion is oriented toward the substrate surface,
   (2) the substrate and the male-type engaging elements both contain a mixture of a polyvinyl alcohol, a polyhydric alcohol- or ethylene oxide-based polymer, and a layered inorganic particle, the polyhydric alcohol- or ethylene oxide-based polymer being mixed in a proportion in the range of 5 to 30 parts by mass and the layered inorganic particle being mixed in a proportion in the range of 3 to 20 parts by mass, based on 100 parts by mass of the polyvinyl alcohol, and
   (3) the polyvinyl alcohol has a degree of polymerization of 300 to 700 and a degree of saponification of 60 to 80% by mole.

2. The water-soluble male-type molded hook-and-loop fastener according to claim 1, wherein when each of the male-type engaging elements has a shape in which the male-type engaging element rises from the substrate surface, curves in mid-course, in the row direction so that a tip portion thereof is oriented toward the substrate surface, the male-type engaging element has a height from the substrate surface to a top of the male-type engaging element of 1.2 mm or less, and when each of the male-type engaging elements has a shape in which the male-type engaging element branches in mid-course forward and backward in the row direction so as to curve in the row direction so that each branched tip portion is oriented toward the substrate surface, the male-type engaging element has a height from the substrate surface to a top of the male-type engaging element of 0.6 mm or less.

3. The water-soluble male-type molded hook-and-loop fastener according to claim 1, wherein the polyhydric alcohol- or ethylene oxide-based polymer is a polyethylene glycol, the polyethylene glycol having a number average molecular weight of 300 to 700.

4. The water-soluble male-type molded hook-and-loop fastener according to claim 1, wherein the layered inorganic particle is talc.

5. The water-soluble male-type molded hook-and-loop fastener according to claim 1, wherein the water-soluble male-type molded hook-and-loop fastener has such a water solubility as to completely dissolve in water of 25° C. within 20 minutes.

6. The water-soluble male-type molded hook-and-loop fastener according to claim 1, wherein 98% or more of the male-type engaging elements each have a tip portion that is oriented toward the substrate surface without ending in mid-course.

7. A combination of the water-soluble male-type molded hook-and-loop fastener according to claim 1 and a water-soluble loop-type hook-and-loop fastener made of a water-soluble fiber.

8. The combination according to claim 7, wherein the water-soluble loop-type hook-and-loop fastener is a nonwoven fabric or woven or knitted fabric made of a polyvinyl alcohol-based fiber, and has loops made of the same polyvinyl alcohol-based fiber on a surface thereof.

9. A method of producing the water-soluble male-type molded hook-and-loop fastener according to claim 1, the method comprising:
pouring a molten product of a mixture that satisfies the following (4) and (5) onto a surface of a metal roll that satisfies the following (A), while press-filling the molten product into cavities each having a male-type engaging element-shape perforated in the metal roll surface,
cooling and solidifying the molten product as it is, and
peeling the solidified product from the metal roll surface while pulling the solidified product out of the cavities,
wherein (A), (4), and (5) are as follows:
(A) the metal roll is thin ring-shaped dies superposed, the thin ring-shaped dies each having a plurality of male-type engaging element-shaped cavities engraved on an outer circumference thereof so that a plurality of cavities for male-type engaging element are arranged in rows on the metal roll surface in a circumferential direction of the roll, and each of the cavities curves in mid-course, in a cavity-row direction so that a tip portion thereof approaches the metal roll surface, or each of the cavities branches in mid-course into two lines so as to curve in the row direction so that each tip portion thereof approaches the metal roll surface,
(4) the mixture contains a mixture of a polyvinyl alcohol, a polyhydric alcohol- or ethylene oxide-based polymer, and a layered inorganic particle, the polyhydric alcohol- or ethylene oxide-based polymer being mixed in a proportion in the range of 5 to 30 parts by mass and the layered inorganic particle being mixed in a proportion in the range of 3 to 20 parts by mass, based on 100 parts by mass of the polyvinyl alcohol, and
(5) the polyvinyl alcohol has a degree of polymerization of 300 to 700 and a degree of saponification in the range of 60 to 80% by mole.

10. The method of producing a water-soluble male-type molded hook-and-loop fastener according to claim 9, wherein when each of the cavities has a shape in which the cavity curves in mid-course, in the cavity-row direction so that a tip portion thereof approaches the metal roll surface, the cavity has a largest depth from the metal roll surface of 1.2 mm or less, and when each of the cavities has a shape in which the cavity branches in mid-course into two lines so as to curve in the row direction so that each tip portion thereof approaches the metal roll surface, the cavity has a largest depth from the metal roll surface of 0.6 mm or less.

11. The water-soluble male-type molded hook-and-loop fastener according to claim 1, wherein said polyvinyl alcohol has a degree of polymerization of 370 to 550.

12. The water-soluble male-type molded hook-and-loop fastener according to claim 1, wherein said polyvinyl alcohol has a degree of saponification of 72 to 78% by mole.

\* \* \* \* \*